_United States Patent_ [19]

Von Fellenberg

[11] Patent Number: 4,627,818

[45] Date of Patent: Dec. 9, 1986

[54] PSYCHOTECHNOLOGICAL TESTING METHOD AND DEVICE THEREFOR

[76] Inventor: Jost Von Fellenberg, Auf der Bürglen 27, 8627 Grüningen, Switzerland

[21] Appl. No.: 769,558

[22] Filed: Aug. 26, 1985

[30] Foreign Application Priority Data

Aug. 28, 1984 [CH] Switzerland ............... 4124/84-5

[51] Int. Cl.$^4$ .............................................. G09B 19/00
[52] U.S. Cl. .................................... 434/236; 434/322; 434/363
[58] Field of Search ................ 434/236, 322, 363, 364

[56] References Cited

U.S. PATENT DOCUMENTS 2,527,469  10/1950  Vernon et al. ...................... 434/322

FOREIGN PATENT DOCUMENTS 7115260  5/1973  Netherlands .

*Primary Examiner*—William H Grieb
*Attorney, Agent, or Firm*—Ostrolenk, Faber, Gerb & Soffen

[57] ABSTRACT

A method and device for determining the disposition, traits or characteristics of human test subjects. Several sets of statements are formulated, each set being related to at least one trait. The statements in a set are divided into two groups which contain several pairs of complementary statements, each pair probing the same point from different perspectives. A test subject provides responses from a multiple choice menu. The responses are considered on a group basis and a weight factor is assigned to each response. Templates are used in which the assigned weighting factors for each response are marked. A score is added up for each group of statements. The sum of points for a given trait, for example, communicative attitudes which are addressed by one statement group, are plotted on an indexed polar coordinate system. Similarly, points derived for the complementary group which deals with the same trait but from a different perspective, i.e., statements that focus on the non-communicative attitudes of the subject, are plotted on another corresponding coordinate system. The polar vectors which represent each trait are vectorially added and the midpoint of the resultant vector is found. The arithmetic average of the vectors provides the value of a radius of a circle which is centered on the mid point of the resultant vector. The circle defines sectors between the axes of the coordinate system. From this, the test subject's traits such as empathy, willingness to learn and sociability, as well as aggressiveness, selfishness, etc., can be determined.

14 Claims, 7 Drawing Figures

The statement is true of me:
1. RARELY OR NEVER
2. NOW AND THEN/OCCASIONALLY
3. FREQUENTLY
4. VERY FREQUENTLY/AS A RULE/MOST OF THE TIME

*Fig-1a*

| | | | | |
|---|---|---|---|---|
| 1. In dealing with a person I am interested in his entire person, i.e. his awareness of life, thoughts, background, etc. | 4 3 2 1 | 2. I prefer to maintain a certain distance and to limit my association with others to the matter at hand. | 4 3 2 1 |
| 3. I tend to remain reserved and play the role which I have to play in society and at work. | 4 3 2 1 | 4. I open myself up completely in an encounter and act the way I really am. | 4 3 2 1 |
| 5. I have a certain reserve about intruding into other people's concerns. | 4 3 2 1 | 6. I believe that I am sympathetic to other people. | 4 3 2 1 |
| 7. I listen attentively during conversations and share in the concerns of the person with whom I'm speaking. | 4 3 2 1 | 8. When talking, I don't like to be distracted and prefer to remain occupied with the matter at hand. | 4 3 2 1 |
| 9. It is easy for me to see the positive side even of people whom I don't like. | 4 3 2 1 | 10. It's hard for me also to see the positive side of people whom I don't like. | 4 3 2 1 |

*Fig. 1b*

| | | | | | |
|---|---|---|---|---|---|
| 11. I sometimes find certain people unlikeable spontaneously. | 4<br>3<br>2<br>1 | 12. I'm easily attracted to other people. | 4<br>3<br>2<br>1 | | |
| 13. Despite differences in opinion I'm open-minded toward people with whom I speak. | 4<br>3<br>2<br>1 | 14. Real differences in opinion can result in a real dislike especially the contrary opinion of the person. | 4<br>3<br>2<br>1 | | |
| 15. I cannot accept people of other races, cultures religions, etc. completely and without reservation. | 4<br>3<br>2<br>1 | 16. I accept people of other races, religions, etc. without reservation. | 4<br>3<br>2<br>1 | | |
| 17. In a quarrel I hardly bother about the feelings of the other party. | 4<br>3<br>2<br>1 | 18. Even in a quarrel I try as far as possible to put myself in the other party's place and appreciate his position. | 4<br>3<br>2<br>1 | | |
| 19. I have no objection if the party with whom I'm speaking knows a few of my weaknesses. | 4<br>3<br>2<br>1 | 20. I am careful in a discussion not to make a fool of myself. | 4<br>3<br>2<br>1 | | |
| 21. I attempt to overcome any feeling of hatred which might arise in me by acceding to the other. | 4<br>3<br>2<br>1 | 22. It can happen that I reject a person completely. | 4<br>3<br>2<br>1 | | |

Fig. 1c

23. I have had personal enmities.

| | 4 |
|---|---|
| | 3 |
| 2 | |
| 1 | |

24. Up to now I've been able to avoid personal enmities.

| | 4 |
|---|---|
| | 3 |
| | 2 |
| | 1 |

PSYCHOTECHNOLOGICAL TESTING METHOD AND DEVICE THEREFOR

BACKGROUND OF THE INVENTION

The present invention relates to a psychotechnological method and device for detecting the traits of human test subjects.

It is desirable to be able to classify individuals according to their traits so that the optimal working place and job functions may be found for them. If carried out successfully, individuals will be satisfied and will be remunerated in accordance with their actual capabilities and demonstrated performance.

Qualification tests and examinations of this type have existed for decades and are constantly being refined. They include psychotechnological procedures which are carried out in order to determine the disposition of such test subjects, in order to establish their suitability, in accordance with the objectives which are set forth above.

The method according to the present invention provides an improvement over known methods which is characterized in that several complexes or sets of statements are formulated, each set being divided into two complementary statement groups. The first of the two groups probes one human trait from one perspective, while the second group contains statements which probe the same human trait from a different, complementary perspective. The test subject is asked to comment by selecting an answer from a list of three or more possible responses. The test subject is judged by his or her responses. The responses are weighted groupwise by means of predetermined weighting factors which produce response scores which are added together per group to provide a group test score. The group test scores associated with the first group of each set are plotted on the numerically graduated axes of a multi-axial polar coordinate system having enough axes to cover the number of complexes or sets of statements. Analogously, the group test scores associated with the second group of each set, which deal with the complementary statements, are plotted on another corresponding polar coordinate system. The values which the test provides are used for evaluating the test subject.

The invention further includes an apparatus for carrying out the foregoing method. The apparatus includes at least one of the following implements:
(A) statement sheets;
(B) evaluation templates;
(C) graduated or indexed polar coordinate system networks with coordinate axes which represent human qualities or traits.

The invention will be explained below by reference to an embodiment thereof in conjunction with the accompanying drawings, in which:

DETAILED DESCRIPTION OF A PREFERRED EMBODIMENT

Figure 1A:
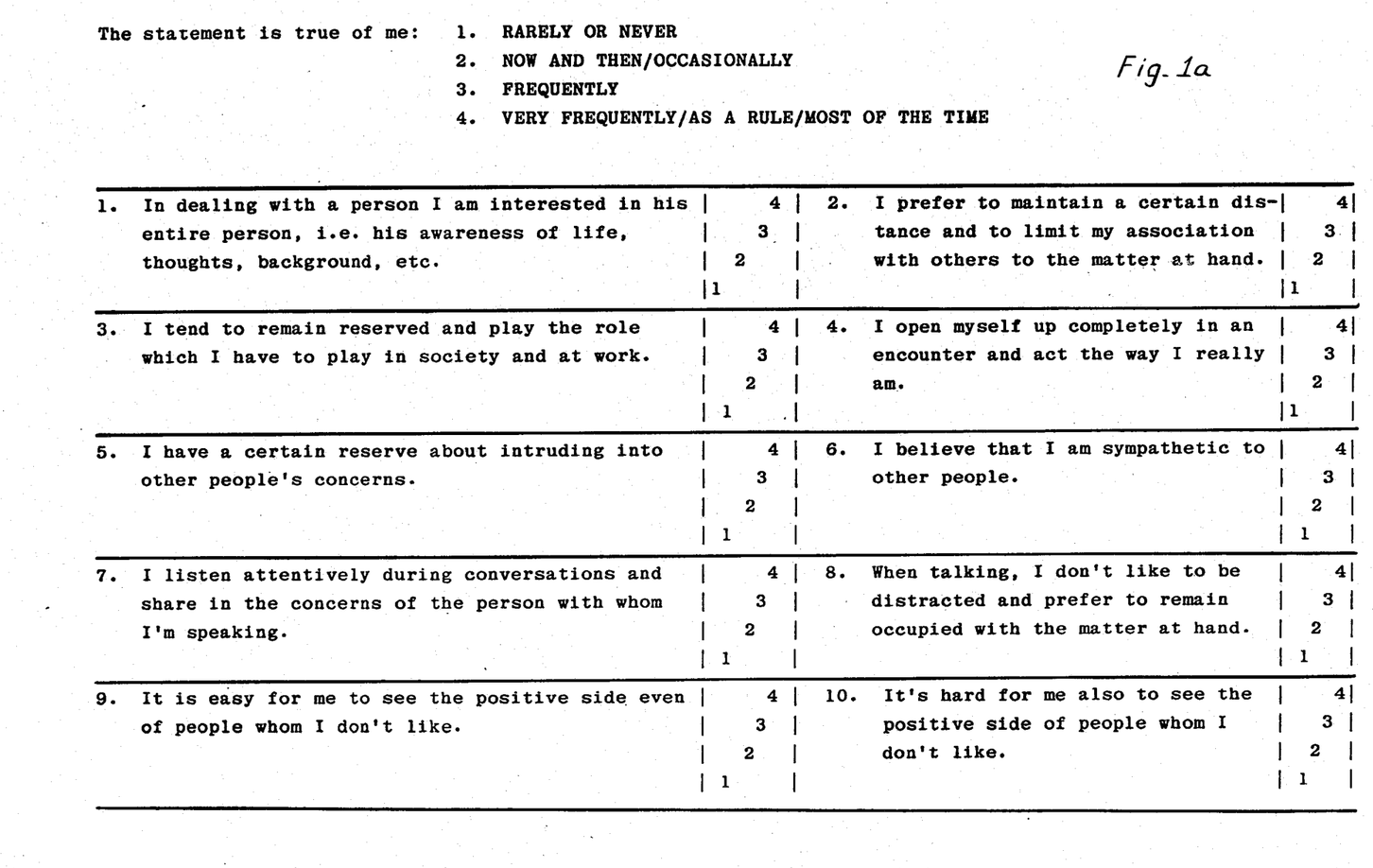
FIGS. 1a–1c show a portion of a model statement sheet which illustrates the manner in which the statements are subdivided into groups.
Figure 1B:
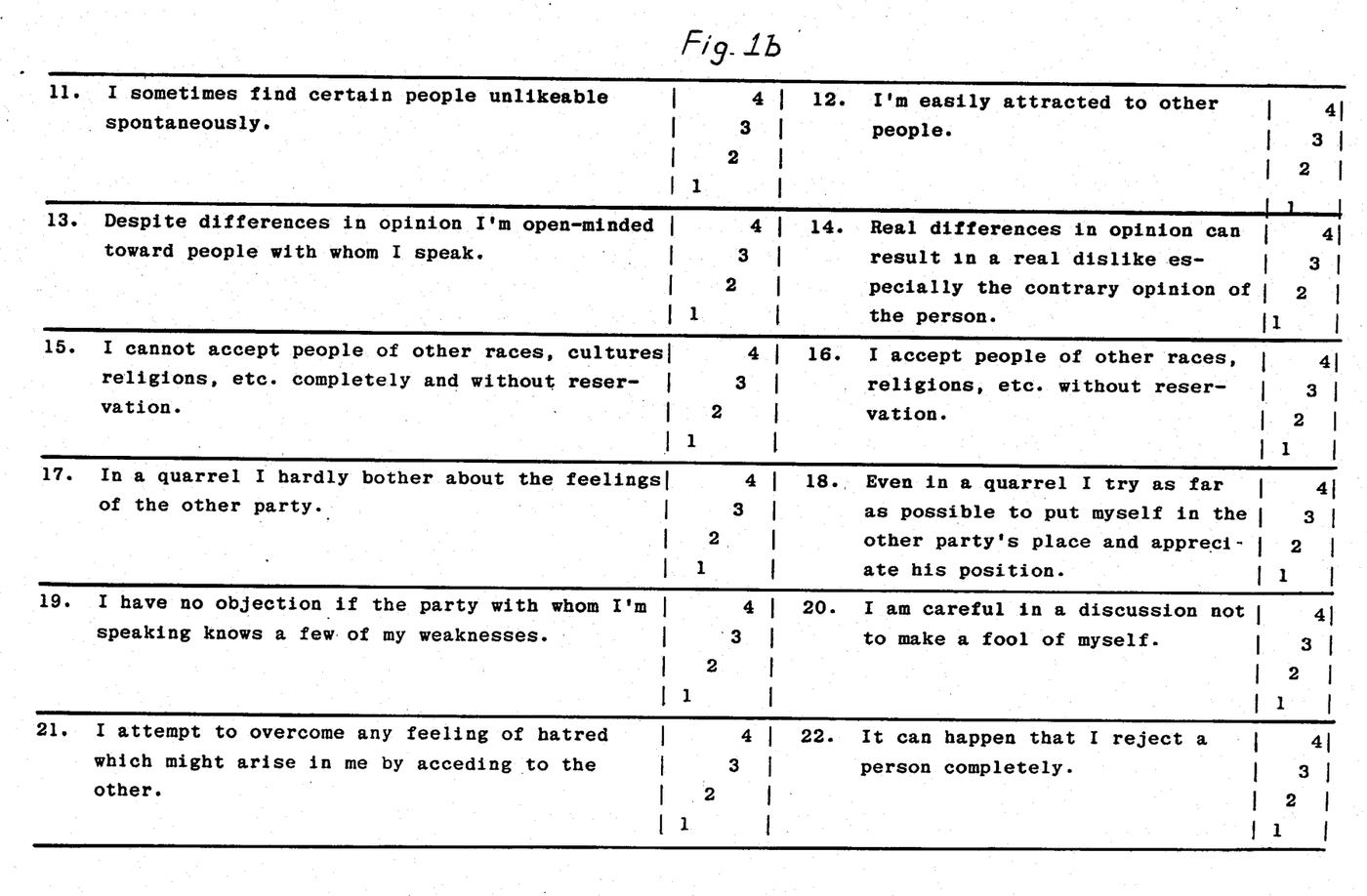
Figure 1C:
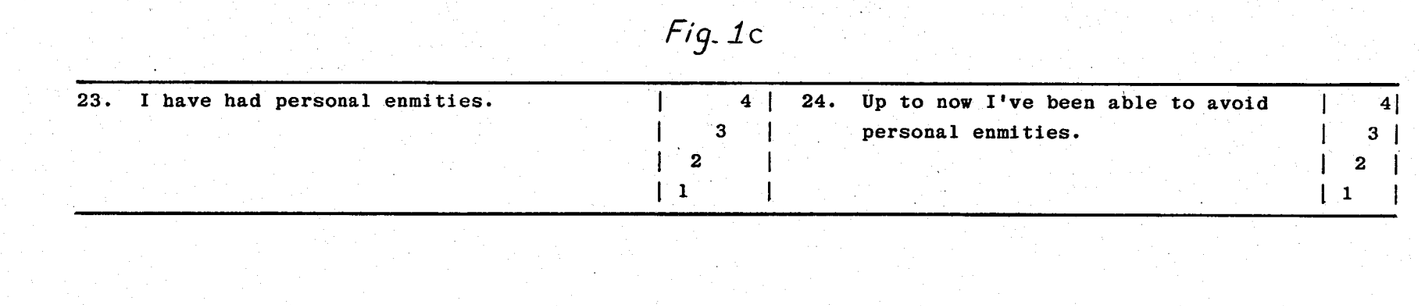

The invention will now be described by reference to a sample problem which is solved by means of the present invention. The test, discussed below, is intended, for instance, to assist in estimating the communicative attitude of a person. For this purpose, pairs of relatively contrasting statements or questions regarding manners, attitudes or conduct are presented, which are not necessarily mutually exclusive of each other. The person being tested will judge the extent to which a given statement is true of him or her. It is natural that, the answers which will be provided depend on the situation, the test subject, the mood, etc., and may vary accordingly. It is also true that, on the average, the answers will tend to reflect the actual behavior of that subject. For this reason, in each case, both sides of the two columns which appear in FIG. 1 are judged simultaneously and in connection with each statement the evaluator will decide which one of four choices of answers reflects the individual under evaluation. Each of the four answers is of a specified type or category, for example, as shown below.

Answer "1" is: this statement is rarely or never true of me;

Answer "2" is: this statement is now and then or occasionally true of me;

Answer "3" is: this statement is frequently true of me;

Answer "4" is: this statement is very frequently, and as rule, most of the time, true of me.

In FIGS. 1a–1c, 24 pairs of statements are set forth. Each odd numbered statement is complementary to the adjacent even numbered statement. In other words, each statement requires and is complemented by another statement, so that statement pairs appear throughout. The pairs of statements differ from each other in viewing a given subject from two different perspectives such as, for example, a glass being half-full or half-empty, or one-third full or two-thirds empty, etc.

Each statement requires a response from the test subject. Four standard responses are provided and a given response is selected by the test subject by marking one of four columns 1, 2, 3, and 4. A mark, for instance an X, in column 1 means, "rarely or never", in column 2, "now and then, occasionally", in column 3 "frequently", and in column 4 "very frequently, and as a rule, most of the time". From the arrangement in FIG. 1 and from the associated statements, it is evident that an individual who responds to a statement located on the left side by marking column 1 is likely to mark colum 4 in response to the corresponding statement located in the right side of the questionnaire. The corresponding statements, for instance statements 1 and 2, are referred to as complementary staements, and the answers to them evidence complementary attitudes. For example, a low interest in one's fellow men can also be expressed by stating that one prefers to maintain a distance from others. These are the two complementary attitudes.

If a person, even while having different opinions, is generally open-minded with regard to those with whom he communicates, he will mark column 4 in response to statement 13. Since, to him, real differences of opinion rarely or never result in dislike of the person with whom he disagrees, he will mark column 1 in response to statement 14 and therefore these two attitudes correspond to one another and are complementary. The statements are thus laid out such that on the one side, column 1 and, on the other side, column 4, correspond to each other, as is also true of columns 2 and 3 and columns 4 and 1. Responses selected from columns 1 and 1 or 4 and 4 from the opposite sides of the page are not compatible to one another.

A thorough test of a subject includes three complexes or sets or statements, each set consists of two groups, the statement in each group being related to one another in a manner similar to the sample statements in FIGS. 1a–1c, i.e., they are complementary to one another.

For the present example, it is assumed that the first set is directed to a first human trait and includes group "a" and "d" ("a" and "d" refer to the two complementary groups of statements); the second set is directed to a second trait and includes groups "b" and "e"; and the third set includes groups "c" and "f".

Statements related to different qualities or traits such as quality groups "a" and "d", or "b" and "e", or "c" and "f" are intermixed in order to avoid influencing the person who is tested in one direction or another. This is illustrated in FIGS. 1a–1c wherein statements 1, 7 and 9 test the communicative attributes of a person and as such belong to quality group "a", while statements 3 and 5 are non-communicative and belong to quality group "d".

Figure 2A:
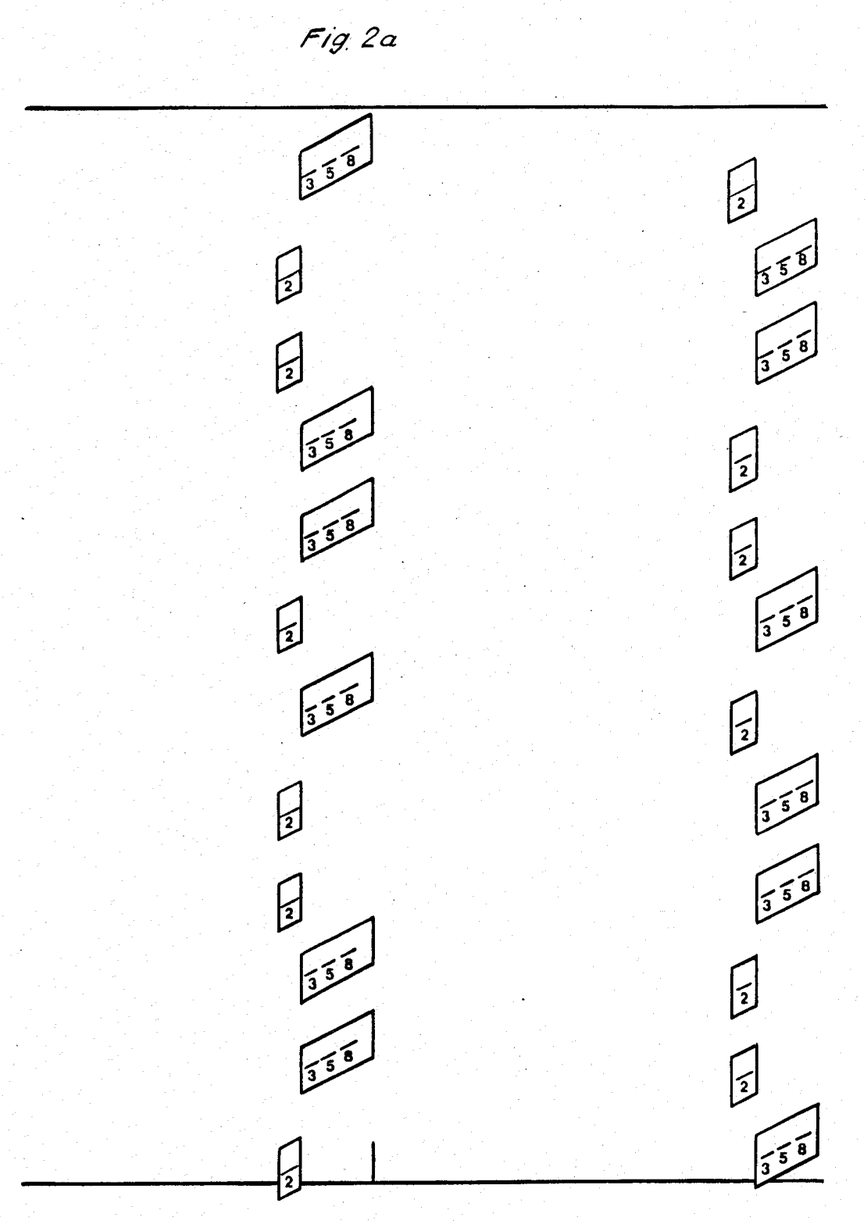
FIGS. 2a and 2b show templates with assigned values marked thereon for scoring the tests.
Figure 2B:
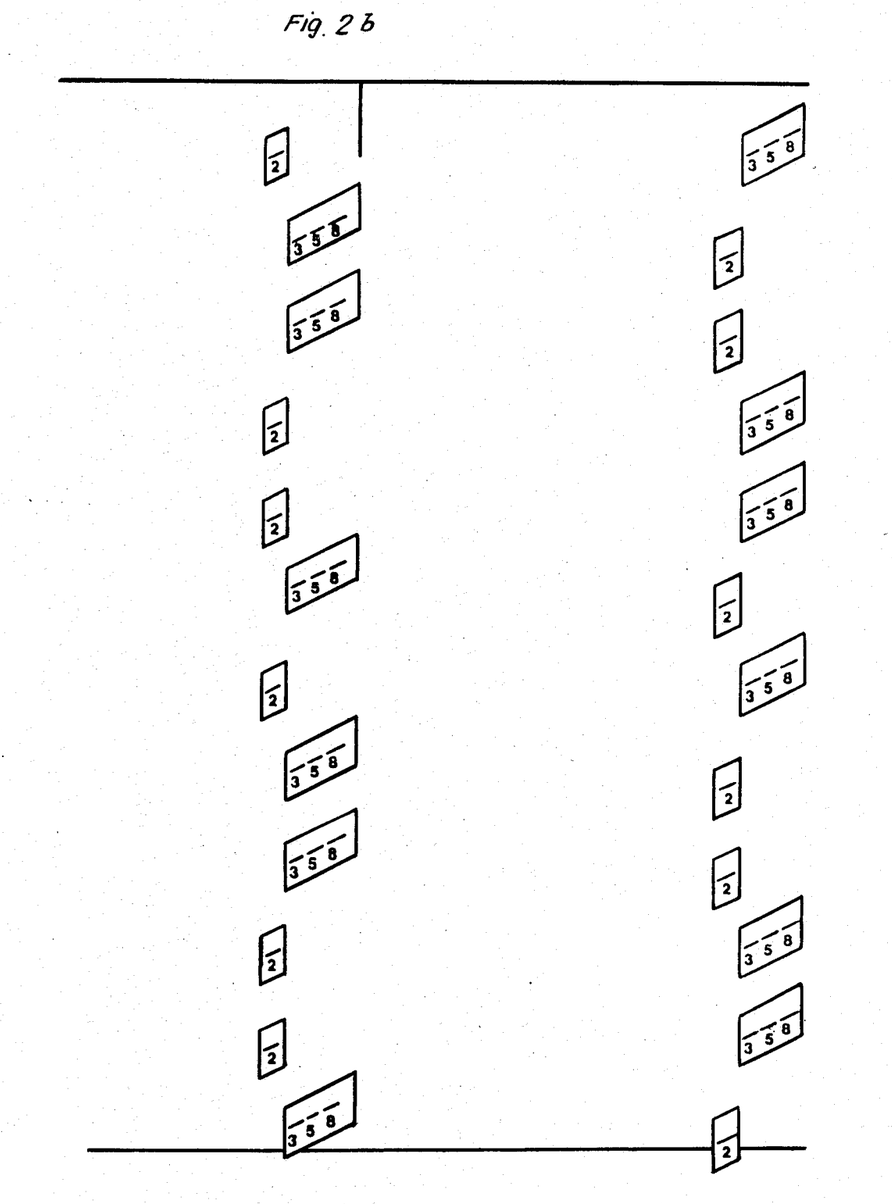

The transparent template which is illustrated in FIG. 2, makes it possible to quickly evaluate the responses related to a given trait, for example the responses to the communicative statements. In this connection, one of templates "a", "b" or "c" ("a" is shown in FIG. 2a) is used to evaluate a given complex or set of communicative statements a, b, or c, and a template is provided for each complex or set of non-communicative statements d, e, f (template "d" is shown in FIG. 2b). Template "a" is constructed such that the communicative statements of columns "2-4" are assigned values 3, 5 and 8 while, for the non-communicative statements, a response in column "1" has a value of 2, while the other columns "2-4" are assigned a value of zero. These templates are placed on the statement sheets. The boxes on the template which show an X are marked on the template and for each template the sum of the assigned values are recorded.

In the example of FIGS. 1a–1c and 2a, the communicative-value template of FIG. 2a is placed on the statement sheet of FIG. 1 and those values marked with Xs on the statement sheet as seen through the template are added and recorded. The sum A* is entered on the bottom of the template. One proceeds in a similar manner with the non-communicative template d. In template d, the values are complementary to template a. The same applies to the pair of templates b, e and c, f.

The above procedure is repeated for the two other complexes or sets of statements relating to quality groups b and e and the quality groups c and f. In this manner the communicative total values A*, B* and C* and the noncommunicative total values D*, E* and F* are derived. With the values A*, B*, C* recorded on templates a, b and c and the values D*, E*, F* recorded on templates d, e and f, two graphs are now drawn over two triaxial polar coordinate systems (FIGS. 3 and 4) which show the tendencies of attitude and traits of the person tested.

Each of the values A*, B* and C*, D*, E* and F* is associated with a respective one of the six axes provided by the two coordinate systems. The system according to FIG. 3 contains the axes a, b and c, and the system according to FIG. 4 contains the axes d, e and f. The six axes are graduated from 0 to 100. The obtained values are plotted on the corresponding axes and the points are marked with an X. A graphical representation of the traits of the test subject is obtained by drawing a circle determined by the values A*, B* and C* and D*, E* and F*, respectively, on the two coordinate systems.

Figure 3:
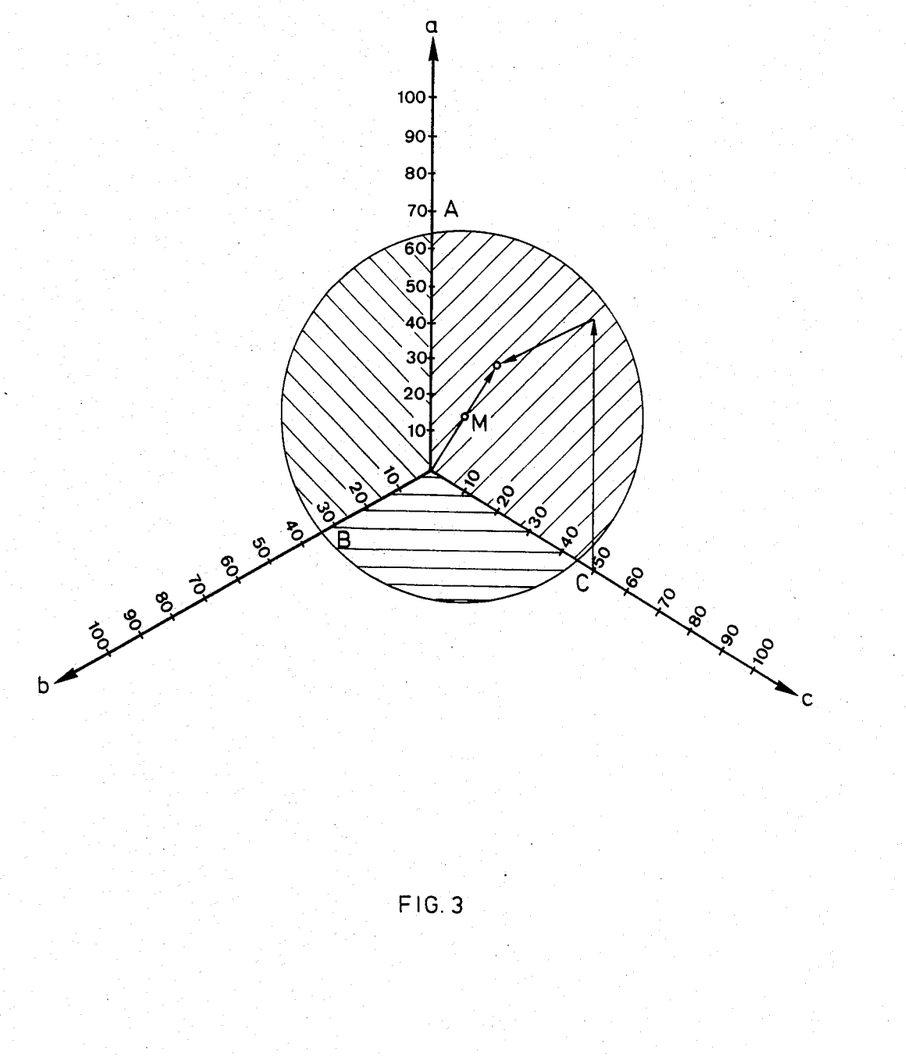
FIG. 3 shows a polar coordinate resonance image in accordance with the invention.
Figure 4:
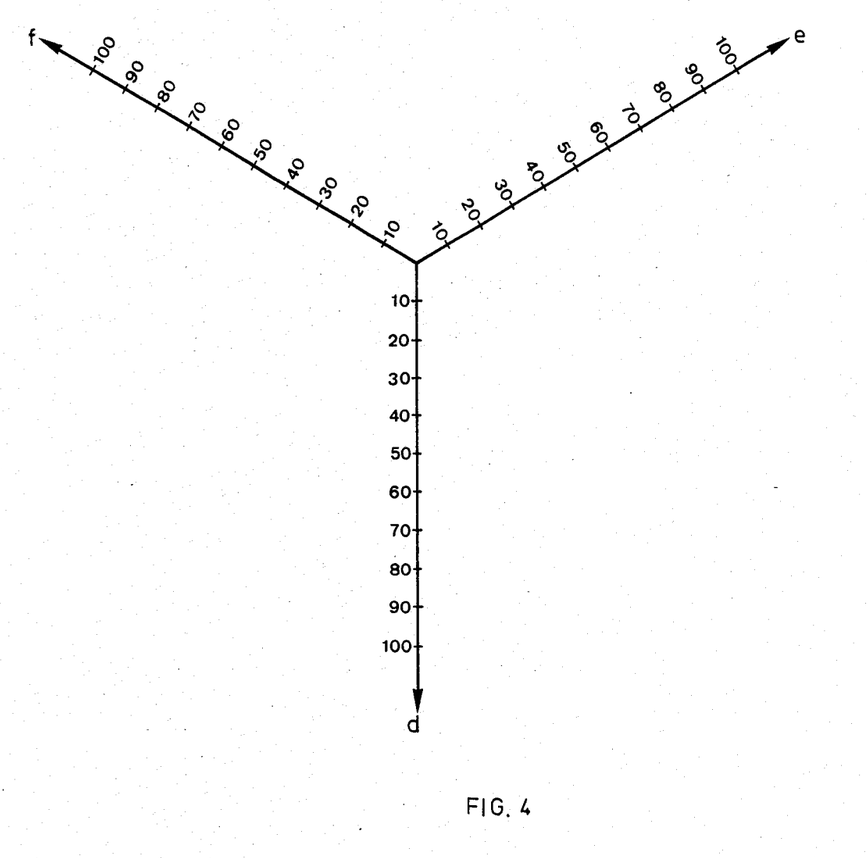
FIG. 4 is similar to FIG. 3 except that complementary attitudes are plotted thereon.

The centers of the two circles associated with the three groups of values are found by adding the three vectors A*, B* and C* and D*, E* and F*, respectively. The midpoint of the resultant vector is the center point M of a circle. The radii of the circles can be calculated as the arithmetic average of the values.

In the coordinate system according to FIG. 3 this yields:

$$r_R = \frac{A^* + B^* + C^*}{3} = \ldots$$

and in the coordinate system according to FIG. 4

$$r_D = \frac{D^* + E^* + F^*}{3} = \ldots$$

These radii can be measured by noting their numerical value on one of the axes and the corresponding circles drawn around the midpoint by means of a compass. The shaded sectors in FIG. 3 convey meaningful data with respect to the test subject. It is, of course, possible to effect the evaluation with other center points and other radii, for instance, by means of geometrical or harmonic mean values, etc.

The position and size of these specific circles provide certain indications as to the disposition of the test subject. For example, each sector may emphasize a different characteristic as shown in FIGS. 3 and 4. The coordinate system of FIG. 3 is for the evaluation of the quality groups "a", "b" and "c" and the coordinate system of FIG. 4 is for the evaluation of the quality groups "d", "e" and "f". The evaluations are based on the complexes or sets of statements which are similar to the statement groups of FIGS. 1a–1c.

For quality groups "b", "c", "e" and "f", corresponding complexes or sets of statements will be prepared which are similar to those appearing in FIGS. 1a–1c.

In accordance with the foregoing method using the indicated devices, it is possible to achieve the purpose of the present invention, namely the determination of the disposition of test subject in a relative reliable manner.

Although the present invention has been described in connection with a preferred embodiment thereof, many other variations and modifications will now become apparent to those skilled in the art. It is preferred, therefore, that the present invention be limited not by the specific disclosure herein, but only by the appended claims.

What is claimed is:

1. A psychotechnological method for detecting the disposition of a human test subject toward a selected trait, said method comprising:
   (a) formulating and presenting to the test subject a plurality of sets of statements, each set containing first and second groups which respectively include first and second complementary statements, and a preselected choice of at least three responses for each statement, the test subject selecting one of the responses in answer to each statement, each response being assigned a respective predetermined weighting factor which determines a response value which is assigned to each response;

(b) adding the response values which correspond to the responses selected by the test subject on a group by group basis to derive for each group a group test score;

(c) plotting the group test scores of each one of the groups that is associated with the first complementary statements on a respective axis of an indexed polar coordinate system having at least as many axes as said number of sets of statements;

(d) plotting the group test scores of each one of the groups that are associated with the second complementary statements on a respective axis of a second indexed polar coordinate system having at least as many axes as as said number of sets of statements; and (e) comparing and evaluating the plotted response values which appear on the first and second coordinate systems to determine the characteristic or disposition of the test subject.

2. A method as in claim 1 in which three sets of statements are used and in which each of the first and second coordinate system comprises three isometrically arranged axes.

3. A method as in claim 1 in which the test subject is presented with a multiple choice of four identical responses for each statement.

4. A method as in claim 3 wherein the responses include the statements: rarely or never; now and then or occasionally; frequently; and, very frequently, and as a rule, most of the time.

5. A method as in claim 2 in which adjacent axes of the first and second coordinate system are set about 120° apart from each other.

6. A method as in claim 1 in which the first group of statements includes communicative statements and the second group of statements includes non-communicative statements and wherein the communicative and non-communicative statements are intermixed with one another.

7. A method as in claim 1 in which the statements are presented on a sheet in accordance with a predetermined arrangement and further comprising the step of superimposing over the sheet evaluation templates which are marked with said predetermined weights and which are adapted for identifying statements which are associated with a given group of statements related to a given trait, and using the templates for adding the response value for obtaining the group test score.

8. A method as in claim 2 in which the statements are presented on a sheet in accordance with a predetermined arrangement and further comprising the step of superimposing over the sheet evaluation templates which are marked with said predetermined weights and which are adapted for identifying statements which are associated with a given group of statements related to a given trait, and using the templates for adding the response value for obtaining the group test score.

9. A method as in claim 1 further comprising the step of vectorially adding the group test scores which are plotted on each coordinate system to generate a resultant vector on each coordinate system and bisecting the resulting vector to find its mid point and for using the mid point for drawing a circle whose radius is mathematically related to the group test scores which are plotted on the coordinate system.

10. A method as in claim 9 in which the radius is equal to about the arithmetic, geometrical or harmonic mean of the group test scores.

11. A method as in claim 1 further comprising using areas in the shape of circle segments, located between adjacent axes of the coordinate systems, whose size is determined by the group test scores, for making judgments about the characteristics or disposition of the test subject.

12. A method as in claim 10, further comprising using areas in the shape of circle segments, located between adjacent axes of the coordinate systems, whose size is determined by the group test scores, for making judgments about the characteristics or disposition of the test subject.

13. An apparatus for effecting psychotechnological evaluation of the disposition of a human test subject toward a selected trait, said apparatus comprising:

a statement sheet containing first and second groups including, respectively, first and second complementary statements, and a preselected choice of at least three responses for each statement, a respective one of the responses being selected by the test subject as an answer to a given statement, the statements appearing on the statement sheet in accordance with a predefined arrangement;

at least one evaluation template which can be fitted over the statement sheet, the evaluation template having predefined response weight factors marked thereon which are applicable to each response on the statement sheet; and scoring sheets which are marked with polar coordinate systems and having coordinate axes which represent human traits, the response values which are obtained by means of the evaluation templates being added up to calculate group test scores, the group test scores being plotted on the coordinate axis and being used for detecting the selected trait of the test subject.

14. An apparatus as in claim 13 in which the apparatus is adapted for recording thereon three sets of statements each of which is divided into said first and second complementary groups, the apparatus further including means for indicating the response to each statement, the means for indicating the response comprising four judgment boxes which may be marked by the test subject to indicate an answer, the evaluation template including means for assigning a weighting factor to each response and means for adding the scores assigned to each response for each group, each of the polar coordinate systems having three axes which are graduated in numbers and on which the group test scores may be marked.

* * * * *